(12) United States Patent
Farrell

(10) Patent No.: US 6,997,182 B2
(45) Date of Patent: Feb. 14, 2006

(54) INFLATABLE RESUSCITATION FACE MASK

(76) Inventor: Graham Farrell, 3 Quamby Road, Ringwood North VIC 3134 (AU)

( * ) Notice: Subject to any disclaimer, the term of this patent is extended or adjusted under 35 U.S.C. 154(b) by 112 days.

(21) Appl. No.: 10/332,535

(22) PCT Filed: Jul. 13, 2001

(86) PCT No.: PCT/AU01/00851

§ 371 (c)(1),
(2), (4) Date: Jul. 14, 2003

(87) PCT Pub. No.: WO02/05882

PCT Pub. Date: Jan. 24, 2002

(65) Prior Publication Data

US 2005/0016532 A1  Jan. 27, 2005

(51) Int. Cl.
*A61M 16/00*  (2006.01)

(52) U.S. Cl. .......................... 128/203.11; 128/202.28; 128/202.29

(58) Field of Classification Search ............ 128/202.28, 128/202.29, 203.11, 206.24, 206.26

See application file for complete search history.

(56) References Cited

U.S. PATENT DOCUMENTS

| | | | | |
|---|---|---|---|---|
| 3,695,264 A | * | 10/1972 | Laeral | 128/202.28 |
| 4,811,730 A | | 3/1989 | Milano | |
| 4,834,085 A | | 5/1989 | Webster, II | |
| 5,121,745 A | | 6/1992 | Israel | |
| 5,146,914 A | * | 9/1992 | Sturrock | 128/203.11 |
| 5,465,712 A | * | 11/1995 | Malis et al. | 128/205.25 |
| 5,469,842 A | * | 11/1995 | Flynn | 128/203.11 |
| 5,975,079 A | | 11/1999 | Hellings et al. | |
| 6,109,263 A | * | 8/2000 | Feuchtgruber | 128/206.28 |
| 6,206,003 B1 | * | 3/2001 | Burch | 128/206.21 |
| 2002/0007832 A1 | * | 1/2002 | Doherty | |

FOREIGN PATENT DOCUMENTS

| | | |
|---|---|---|
| EP | 0 455 401 A1 | 11/1991 |
| WO | WO 94/07555 | 4/1994 |

* cited by examiner

*Primary Examiner*—Mital Patel
(74) *Attorney, Agent, or Firm*—Stites & Harbison PLLC; Ross F. Hunt, Jr.

(57) ABSTRACT

An inflatable resuscitation face mask comprising a top sheet joined to a bottom sheet to form an inflatable pocket which when inflated forms a raised body having an apex and a lower perimeter, wherein inflation means is provided on the mask and an opening at the apex allows air to be administered through the opening to an area underneath the inflated mask.

15 Claims, 2 Drawing Sheets

INFLATABLE RESUSCITATION FACE MASK

This invention relates to a device, specifically a face mask, used for resuscitation, that reduces personal contact and possible cross contamination.

Cardio-Pulmonary Resuscitation (CPR) training is becoming increasingly popular in today's society as more members of the community value the advantages of acquiring the required skills in the process of saving lives. Our society now embraces this opportunity but is still hesitant to apply resuscitation when needed due to the fear of contamination by transmission of debilitating and possibly fatal viruses and bacterial infections.

There exists some devices that have attempted to deal with this issue. These devices fit into the following two categories.

The first type of device is the lay over plastic sheet with a non-return ventilation valve that is compact enough to be carried by the rescuer but only allows the ventilation to occur through the patient's mouth. This device does not lift the rescuer above the patient but only acts as a single layer barrier between the rescuer and the patient. The device is light and highly sensitive to breezes and air turbulence often folding up upon itself resulting in possible cross contamination. These devices do not install a sense of confidence in performing the required CPR task often resulting in tragedy.

The second type of device that is commonly used is the plastic injection moulded mask with a one way ventilation valve that covers the patient's nose and mouth. It is not small enough to be easily carried by the person to the scene. These devices are often not used for the set purpose as they are not readily available at the critical moment in time when CPR should be applied. The fear of possible cross contamination reduces the rescuer's willingness to proceed without any form of protective barrier resulting in reduced or no assistance for the patient.

SUMMARY OF THE INVENTION

These problems are overcome by the present invention which provides an inflatable resuscitation face mask comprising a top sheet joined to a bottom sheet to form an inflatable pocket which when inflated forms a raised body having an apex and a lower perimeter, wherein inflation means is provided on the mask and an opening at the apex allows air to be administered through the opening to an area underneath the inflated mask.

The opening at the apex of the raised body is preferably provided with a one-way valve to allow the administration of air in only one direction, namely through the opening to the area underneath the inflated mask.

For reinforcing the conical shape of the inflated mask, it is preferable to provide ribs vertically located around the raised body and extending between the apex and perimeter. The ribs are formed by joining the top and bottom sheets along a rib section.

In the preferred embodiment the ribs extend only part way between the apex and perimeter terminating at a point spaced from the perimeter such that an annular cushion of air is formed at the perimeter when the mask is inflated.

An inflation valve is preferably located on the top sheet to allow for inflation of the mask by the supply of air to the pocket. The mask is preferably formed from soft plastics and can therefore be folded into a compact area when deflated.

In one form of the invention, the mask has an eyelet on either side to include an elasticized or adjustable strap to be attached to secure the mask to the patient.

Another form of the invention, the mask has a saddle attached to the non return ventilation valve to include an elasticized or adjustable strap to be attached to secure the mask to the patient.

The present invention also provides an inflatable resuscitation face mask pack comprising:

a top sheet joined to a bottom sheet to form a inflatable pocket which when inflated forms a raised body having an apex and a lower perimeter, wherein inflatable means is provided on the mask and an opening at the apex allows air to be administered through the opening to an area underneath the inflated mask; and a container for storing the mask therein when deflated and folded.

BRIEF DESCRIPTION OF THE DRAWINGS

To assist with the understanding of the invention reference will now be made to the accompanying drawings.

DETAILED DESCRIPTION OF PREFERRED EMBODIMENT

The present inflatable face mask is used for the performance of First Responder Patient Resuscitation in an emergency. The mask is compact and formed from soft plastic. It comprises a moulded one way ventilation valve to reduce personal contact and possible fluid and particle exchange between patient and rescuer. The mask comprises a pocket which when inflated forms a raised body. An opening at the apex of the raised body allows air to be administered through the opening to the mouth and nasal regions of a patient underneath the inflated mask.

Figure 1:
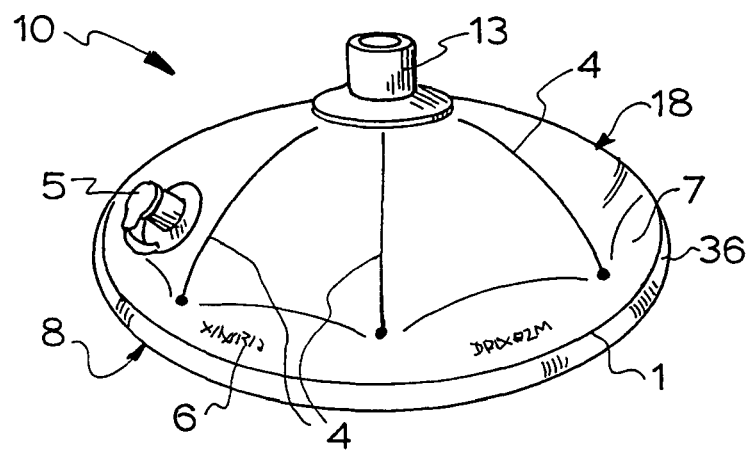
FIG. 1 shows an inflatable face mask according to an embodiment of the invention.

Referring to the Figures and particularly FIG. 1, it can be seen that the inflatable mask 10 is made of a top sheet 7 and a bottom sheet 8 of soft plastic joined together to form a pocket which is inflated to form the raised body 18. In the preferred embodiment the raised body is conical in shape. The top and bottom sheets are joined at a perimeter seam 36 on the annular lower perimeter, or circumference 1. They are also joined together at the top, or apex, of the inflated mask at the centrally located one way ventilation valve 13. A series of vertical contact joints 4, or ribs, join together the top and bottom sheets. The ribs run up and down the mask from the centrally located one way ventilation valve 13 to close the perimeter 1 of the mask. An inflation valve 5 sits on the side of the mask. The mask has printed information in various positions 6 on the plastic sheets.

Figure 2:
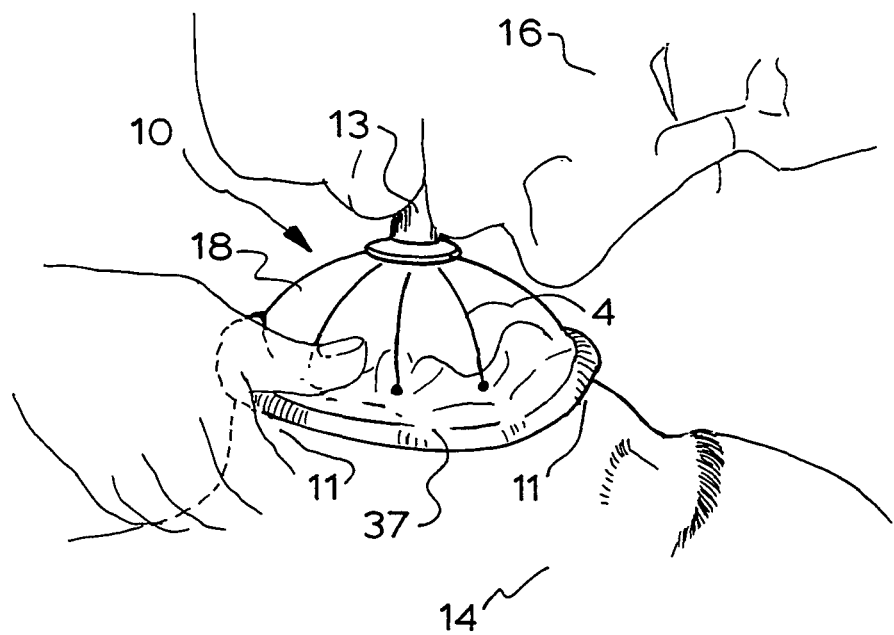
FIG. 2 shows the application of the inflatable face mask by a rescuer on a patient.

Referring to FIG. 2, it can be seen that the inflated mask fits snuggly over the patient's face allowing for both nasal and mouth resuscitation. The rescuer 16 holds the mask in position over the nasal and mouth region and blows into the ventilation one way valve 13 to apply CPR to the patient 14. The mask's conical shape lifts the rescuer above the patient distancing the rescuer from the patient.

The lifting of the ventilation valve is achieved as the twin-skinned, that is double sheeted, device has a circular or elliptical shape with the series of vertical contact joints that act as ribbing support. On inflation these ribs are emphasized as the air is forced between them resulting in a firm uplifted cone shape.

The lower edge of the present device is allowed by design to hold air on inflation resulting in a cushion ring 37 that circumnavigates the complete device. This soft plastic cushion fits firmly across the bridge of the nose, around the cheek area and across the chin. The soft plastic cushion seals the area easily when held in position by the rescuer ensuring maximum effectiveness of ventilation through both the nose and the mouth as required.

The ventilation valve is the only point of contact for the rescuer to apply their mouth to perform CPR. The valve closes off when the patient exhales reducing the possibilities of cross contamination. The one way ventilation valve can be made of any suitable material that can be used to construct an effective mechanism, such as moulded plastic.

The device is made of soft plastic sheeting with basic usage instructions and an additional inflation valve situated on the device.

Figure 3A:
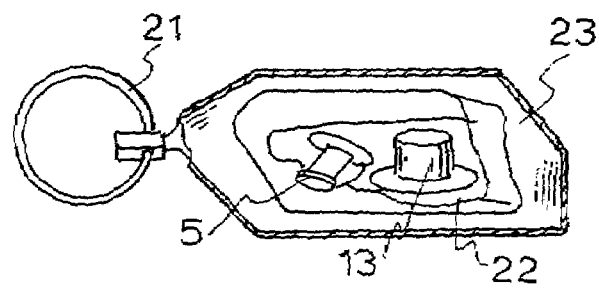
FIG. 3a shows a cross sectional view of the mask folded and packed.
Figure 3B:
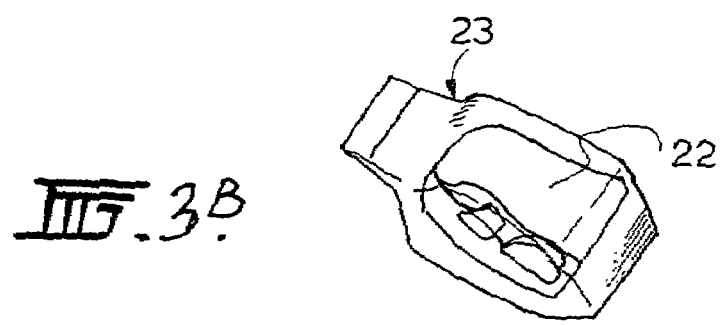
FIG. 3b is a perspective view of the packed mask.

FIGS. 3a and 3b display a keyring 21 incorporating the mask folded and packed, and demonstrates the relative size and compactness of the mask. The mask in its deflated form 22 is folded so as to fit inside a small, compact package 23. This package can be attached to a keyring, belt, placed in pocket, purse or glove box or otherwise on the person in order to be available to the rescuer to meet any possible resuscitation requirements.

Figure 4:
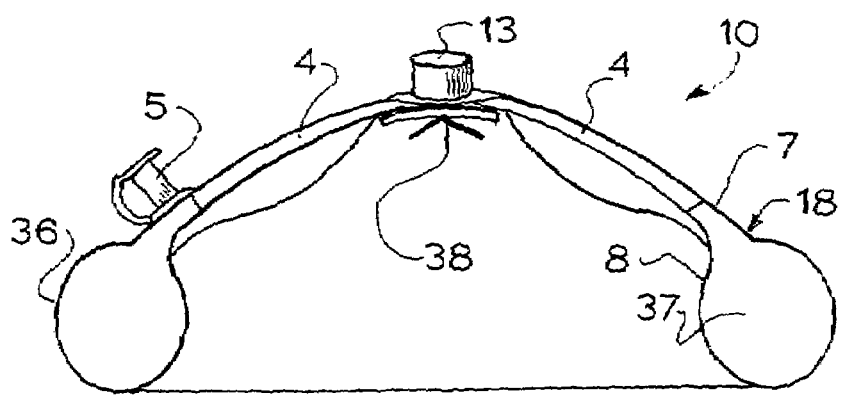
FIG. 4 shows the inflatable face mask in cross section.

The mask 10 is inflated by blowing into the inflation valve 13 allowing for air to fill between the top sheet 7 and the bottom sheet 8. FIG. 4 shows an inflated mask in cross section. The ribs 4 allow for inflation of the conical body 18 which lifts the rescuer's mouth away from the patient. The ribs 4 do not continue all the way to the perimeter seam 36 where the top and bottom sheets join and thereby allow for a cushion of air 37 to exist, this cushion resting on the patient's face and assisting to form an air seal underneath the mask. The one way ventilation valve 13 is located at the top of the mask and has a single direction mechanism 38 to assist in the prevention of the back flow of any fluid or particles through the valve from the patient to the rescuer.

The present device is easily carried on an individual as it is capable of being folded into a size that is small enough to be carried in a purse, a key-ring holder, pocket, car accessories area, neck chain and satchel or as a belt fixture. At the same time the device also inflates to a full size resuscitation mask that allows the patient to be ventilated both through their nose and their mouth. The inflated mask lifts the rescuer above the patient thereby providing an air barrier distancing the rescuer from the patient. Incorporating the one way ventilation valve at the top of the mask also prevents direct contact between the rescuer and patient.

It will be understood to persons skilled in the art of the invention that many modifications may be made without departing from the spirit and scope of the invention. For example, in another embodiment of the invention the mask has eyelets on either side to which an elasticized or adjustable strap is attached for securing the mask to the patient. Alternatively, a saddle attached to the non return valve retains the elasticized or adjustable strap which can be used to secure the mask to the patient.

What is claimed is:

1. An inflatable resuscitation face mask comprising:
   a top sheet joined to a bottom sheet to form an inflatable pocket which when inflated forms a self-supporting raised body that is inflated substantially from an apex of the raised body to a lower perimeter;
   inflation means provided on the pocket and an opening at the apex to allow air to be administered through the opening to an area underneath the inflated mask; and
   ribs located on the raised body and joining the top and bottom sheets together to define a plurality of air passages between the ribs which extend from the lower perimeter of the raised body to the apex of the raised body and into which air is forced when the mask is inflated;
   wherein in its deflated state the mask is capable of being folded.

2. A mask according to claim 1 wherein a one-way valve is provided at the opening allowing only the administration of air in a direction through the opening to the area underneath the inflated mask.

3. The mask according to claim 1 wherein the ribs are located longitudinally on the raised body between the apex and the lower perimeter.

4. The mask according to claim 1 wherein the rids extend only part way between the apex and lower perimeter, terminating at a point spaced from the lower perimeter such that an annular cushion of air is formed at the lower perimeter when inflated.

5. The mask according to claim 1 wherein the lower perimeter is annular and the raised body is conical when inflated.

6. The mask according to claim 1 wherein the inflation means is an inflation valve located on the top sheet which provides access for air into the pocket.

7. The mask according to claim 1 wherein the mask is formed from soft plastics such that the mask can be folded into a compact area when deflated.

8. An inflatable resuscitation face mask pack comprising:
   a top sheet joined to a bottom sheet to form an inflatable pocket which when inflated forms a self-supporting raised body that is inflated substantially from an apex of the raised body to a lower perimeter;
   inflation means provided on the pocket and an opening at the apex to allow air to be administered through the opening to an area underneath the inflated mask; and
   ribs located on the raised body and joining the top and bottom sheets together to define a plurality of air passages between the ribs which extend from the lower perimeter of the raised body to the apex of the raised body and into which air is forced when the mask is inflated;
   wherein in its deflated state the mask is capable of being folded; and
   a container for storing the mask therein when deflated and folded.

9. The mask pack according to claim 8 wherein the container forms part of a key ring, neck chain or any other convenient carry means.

10. A mask pack according to claim 8 wherein a one-way valve is provided at the opening allowing only the administration of air in a direction through the opening to the area underneath the inflated mask.

11. The mask pack according to claim 8 wherein the ribs are located longitudinally on the raised body between the apex and the lower perimeter.

12. The mask pack according to claim 8 wherein the ribs extend only part way between the apex and lower perimeter, terminating at a point spaced from the lower perimeter such that an annular cushion of air is formed at the lower perimeter when inflated.

13. The mask pack according to claim 8 wherein the lower perimeter is annular and the raised body is conical when inflated.

14. The mask pack according to claim 8 wherein the inflation means is an inflation valve located on the top sheet which provides access for air into the pocket.

15. The mask pack according to claim 8 wherein the mask is formed from soft plastics such that the mask can be folded into a compact area when deflated.

* * * * *